US012710367B2

(12) United States Patent
Iyer

(10) Patent No.: US 12,710,367 B2
(45) Date of Patent: Aug. 18, 2026

(54) SYSTEMS FOR NANOPLASTICS DETECTION AND METHOD OF USING THE SAME

(71) Applicant: Vidhatri L. Iyer, Zionsville, IN (US)

(72) Inventor: Vidhatri L. Iyer, Zionsville, IN (US)

( * ) Notice: Subject to any disclaimer, the term of this patent is extended or adjusted under 35 U.S.C. 154(b) by 116 days.

(21) Appl. No.: 18/931,616

(22) Filed: Oct. 30, 2024

(65) Prior Publication Data

US 2025/0146938 A1 May 8, 2025

Related U.S. Application Data

(60) Provisional application No. 63/547,211, filed on Nov. 3, 2023.

(51) Int. Cl.

*G01N 21/64* (2006.01)
*G01N 1/40* (2006.01)
*G01N 33/18* (2006.01)

(52) U.S. Cl.

CPC ......... *G01N 21/643* (2013.01); *G01N 1/4077* (2013.01); *G01N 33/18* (2013.01); *G01N 33/1813* (2013.01); *G01N 2001/4088* (2013.01); *G01N 2021/6439* (2013.01); *G01N 33/1826* (2013.01)

(58) Field of Classification Search

CPC .... G01N 1/4077; G01N 21/643; G01N 33/18; G01N 33/1813; G01N 33/1826; G01N 2001/4088; G01N 2021/6439

See application file for complete search history.

(56) References Cited

U.S. PATENT DOCUMENTS

| | | | | |
|---|---|---|---|---|
| 2019/0204224 | A1* | 7/2019 | Murcia | G01N 21/643 |
| 2022/0228964 | A1* | 7/2022 | Knox | G01N 15/1425 |
| 2023/0285969 | A1* | 9/2023 | Khoo | B01L 3/502761 |
| 2025/0020569 | A1* | 1/2025 | Prater | G01N 15/1434 |

OTHER PUBLICATIONS

Iskandarani, S., Manjunath, S., Busquets, R., Raeli, L., Saikaly, P. E., & Campos, L. C. (2025). "Characterization of nanoplastics and small-sized microplastics in sewage treatment." Scientific reports, 15(1), 30089. https://doi.org/10.1038/s41598-025-15504-9 (Year: 2025).*

Vidhatri L. Iyer, "A Novel Rapid Technique for Nanoplastic Detection in Water Samples", Indiana Water Summit, Indianapolis, IN, Sep. 8, 2022, 15 pages.

Vidhatri L. Iyer, "A Rapid One-step Field-based Detection Method for Nanoplastics in Water", International Journal of High School Research, vol. 5, Issue 4, Aug. 2023, 5 pages.

Vidhatri L. Iyer, "Nanoplastics Detection Method in Wastewater", NewsLeaks, Summer 2023, pp. 28 and 29, available online from https://issuu.com/kelmanonline/docs/in_newsleaks_summer2023_issuu?fr=sMWNiNzExNDM3MA, 1 pages.

* cited by examiner

*Primary Examiner* — Mark R Gaworecki

(74) *Attorney, Agent, or Firm* — Barnes & Thornburg LLP

(57) ABSTRACT

A method of detecting nanoplastics in water includes collecting a water sample from the water. The method includes filtering the water sample to remove debris from the water sample to form a filtered water sample. The method includes adding a lipophilic fluorescent dye to the filtered water sample to form a mixture. The method includes incubating the mixture for an incubation time period at a predetermined temperature. The method includes measuring a nanoplastics concentration in the mixture using a measurement device at a predetermined wavelength.

12 Claims, 11 Drawing Sheets

One-Step Sample Analysis

Filter water with 0.4 μm syringe

160 μL of water sample to tube

Add 40 μL of Dye (final conc is 8 μM)

10 min incubation

Read at 450 nm

| Time (min) | Nile Red | |
|---|---|---|
| | Slope | $R^2$ |
| 10 | 971.88 | 0.995 |
| 20 | 933.66 | 0.991 |
| 30 | 964.9 | 0.990 |
| 60 | 1003.6 | 0.990 |

FIG. 3

One-Step Sample Analysis

Filter water with 0.4 μm syringe

160 μL of water sample to tube

Add 40 μL of Dye (final conc is 8 μM)

Read at 450 nm

| Day | Suspended Solids - mg/L | |
|---|---|---|
| | Influent | Effluent |
| 1 | 214 | 6.5 |
| 2 | 244 | 5.1 |
| 3 | 280 | 4.4 |
| 4 | 220 | 6.1 |
| 5 | 164 | 5.2 |

FIG. 6A

| Day | pH | | Phosphorus (mg/L) | | Ammonia (mg/L) | |
|---|---|---|---|---|---|---|
| | I | E | I | E | I | E |
| 1 | 7.20 | 7.53 | 4.38 | 0.816 | 25.7 | 0.058 |
| 2 | 7.58 | 7.55 | 3.94 | 1.385 | 24.8 | 1.085 |
| 3 | 7.30 | 7.63 | 4.14 | 0.951 | 24.2 | 0.500 |
| 4 | 7.32 | 7.64 | 4.15 | 0.633 | 24.6 | 0.046 |
| 5 | 7.29 | 7.57 | 6.28 | 0.953 | 23.2 | 0.036 |

Legends: I -Influent; E- Effluent

FIG. 6B

| Nanoplastics (μg/ml) | Nanoparticles (x $10^{14}$/ml) |
|---|---|
| 80.6 | 293.3 |
| 50.1 | 182.2 |
| 68.4 | 248.9 |
| 59.2 | 215.5 |
| 62.3 | 226.6 |

FIG. 8

| Month | Suspended Solids - mg/L | |
|---|---|---|
| | Influent | Effluent |
| 1 | 266.4 | 3.3 |
| 2 | 379.2 | 3.8 |
| 3 | 177.6 | 3.0 |
| 4 | 298.4 | 3.0 |
| 5 | 367.2 | 4.0 |
| 6 | 420.0 | 4.6 |

SYSTEMS FOR NANOPLASTICS DETECTION AND METHOD OF USING THE SAME

CROSS REFERENCE TO RELATED APPLICATIONS

This application claims priority to and the benefit of U.S. Provisional Patent Application No. 63/547,211, filed 3 Nov. 2023, the disclosure of which is now expressly incorporated herein by reference.

BACKGROUND

The present disclosure relates to detection systems, and particularly to detection systems for plastics. More particularly, the present disclosure relates to detection systems for nanoplastics.

SUMMARY

The present disclosure may comprise one or more of the following features and combinations thereof.

A method of detecting nanoplastics in water is provided herein. The method may comprise collecting a water sample from the water. The water may be wastewater. The method may comprise filtering the water sample to remove debris from the water sample to form a filtered water sample. The method may comprise adding a lipophilic fluorescent dye to the filtered water sample to form a mixture. The method may comprise incubating the mixture for an incubation time period at a predetermined temperature. The incubation time period may be less than 20 minutes. The method may comprise measuring a nanoplastics concentration in the mixture using a measurement device at a predetermined wavelength.

BRIEF DESCRIPTION OF THE DRAWINGS

FIG. 3 is table showing the effect of incubation times on the slope of linear regression at 620 nm;

FIG. 6A is a table showing influent and effluent water quality;

FIG. 6B is a table showing influent and effluent water quality;

FIG. 8 is a table comparing the nanoplastic content of influent samples;

DETAILED DESCRIPTION

The present disclosure relates to a detection system for nanoplastics in water and methods related to the same. Plastics are widely used because of its low manufacturing cost, durability, and versatility in consumer goods. Plastic waste has caused environmental concern due to the contamination of soil and water bodies, such as rivers and oceans. Moreover, plastics may adsorb toxic aromatic hydrocarbons, heavy metals, and pharmaceutical and personal care products and serve as reservoirs for such toxic agents. Microplastics and nanoplastics may pose health issues such as inflammation and damage to lung epithelial cells. Quantification and tracking of plastic pollution may be complicated due to the trapping of debris in complex matrices, such as wastewater samples.

Small plastic fragments are generated due to the action of chemical and environmental agents, such as soil fungi. Commonly used household products, packaging materials, clothing, and bath scrubs release many plastic fragments into wastewater reservoirs. Plastic fragments with a size of greater than 100 nm and less than 5 mm are characterized as microplastics, and plastic fragments with a size of less than 100 nm are characterized as nanoplastics. Microplastics and nanoplastics in river streams and oceans may harm aquatic life and human health.

Microplastics are hydrophobic and may be visualized by staining the sample containing the microplastics with lipophilic fluorescent dyes, such as, but not limited to, Nile Red. The interaction of the plastics with the fluorophores is facilitated in the presence of organic solvents such as chloroform, acetone, and/or methanol, among others. Staining protocols may be conducted with different microplastics using a filter paper method and quantifying the particles by visual or semi-automated counting techniques. The Nile Red method has proven effective in staining several plastic types, including polyethylene, polypropylene, and polystyrene. However, these staining protocols often involve several steps of sample preparation, washing, and data capture.

Figure 1:
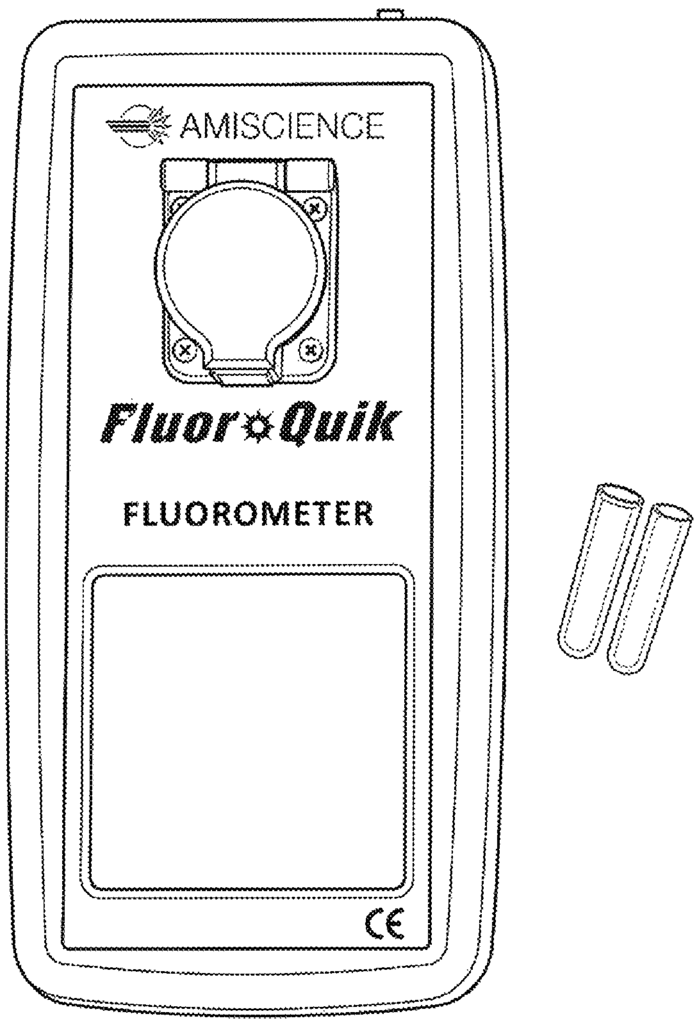
FIG. 1 is a view of a hand-held fluorometer instrument.

Identification of potential hotspots of nanoplastics contamination may be challenging due to a lack of field-based detection methods. A one-step nanoplastic detection method suitable for field applications is provided herein. A hand-held portable fluorometer instrument, as shown in FIG. 1, with an excitation/emission wavelength of 450/620 nm is used with commercial 50 nm polystyrene nanoplastic beads to optimize various assay parameters such as linearity of signal, effects of shaking, and assay incubation times. After optimization of the assay conditions, field samples from influent and effluent wastewater samples are filtered using a 0.45 mm syringe before staining the sample with Nile Red dye in the presence of 20% methanol.

The fluorometer instrument, as shown in FIG. 1, is configured to read a single wavelength with excitation/emission wavelengths of 450/620 nm. The instrument includes a touch-screen LCD display and operates with either a 5V DC power adaptor or four AA batteries. Signals are read by the instrument as relative fluorescent units (RFU) and converted to relevant plastics concentrations using a standard curve with 50 nm polystyrene beads.

The method of detecting nanoplastics uses Nile Red dye, glass tubes (6 mm outer diameter and 300 mm length), eppendorf tubes, 1 ml tuberculin syringes, technical grade methanol, 0.45 μM syringe filters (Hydrophobic PTFE fluorophore), and polystyrene nanoplastic beads of 50 nm. A stock solution of 10 mM Nile Red is prepared using methanol. A working solution of 40 μM Nile Red in methanol is used in the method. Polystyrene beads are adjusted to 400 μg/mL concentration in Milli-Q water, and 1:1 dilutions of beads in water are prepared for a standard curve analysis. The reaction mixture is prepared by transferring 160 μL of water sample with 40 μL of Nile Red working solution (final volume 200 μL) to the glass tubes to maintain a 20% final methanol concentration in the mixture. The samples are incubated for 10 minutes at room temperature. For standard curve analysis, increasing concentrations of known bead solutions are mixed with Nile Red working solution. Blank samples are prepared by mixing Milli-Q water with Nile Red dye in a ratio similar to that of the experimental samples. Glass tubes are inserted into the fluorometer, and data is read at excitation/emission wavelengths of 450/620 nm. The detection may be made within about 10 minutes with a limit of detection of about 35 μg/mL.

Figure 2:
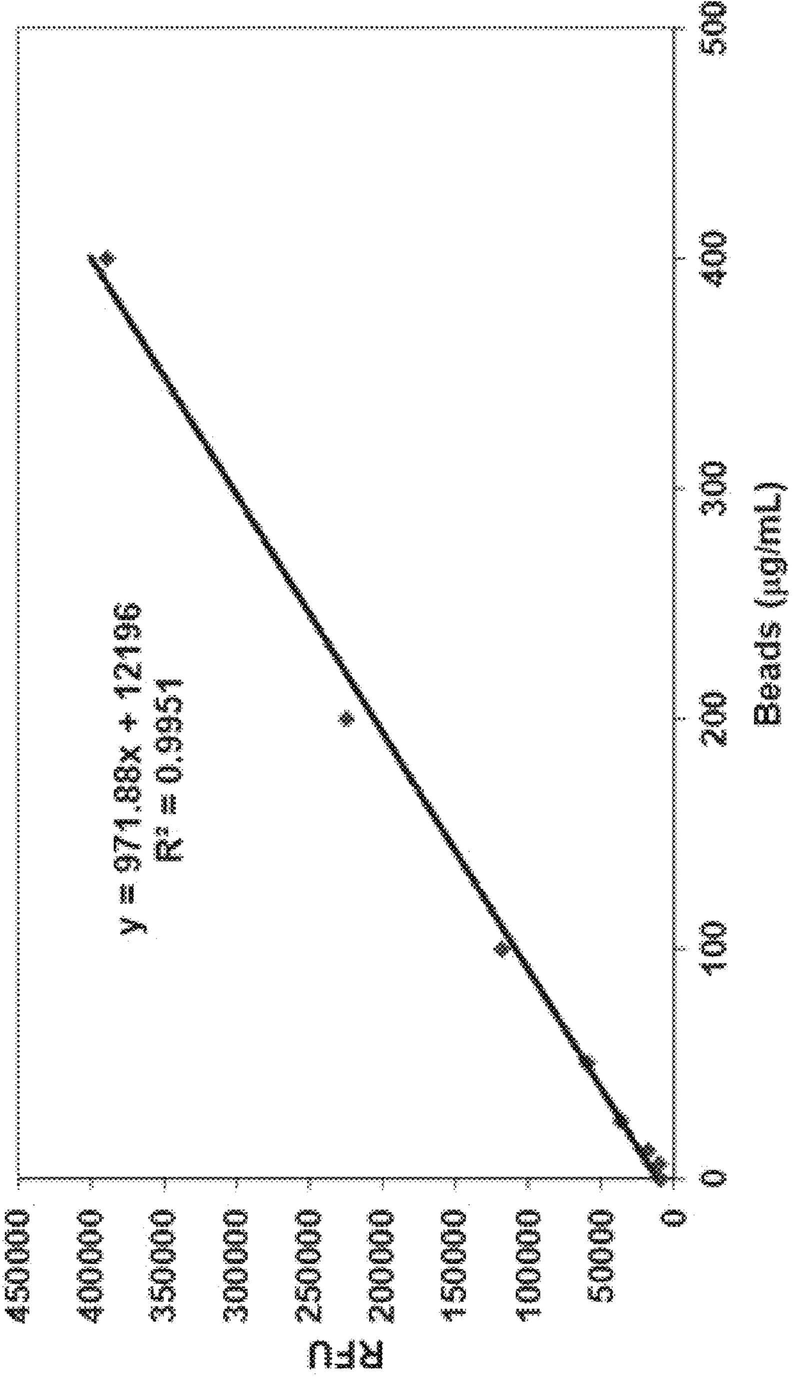
FIG. 2 is a calibration curve prepared using polystyrene beads.

Calibration curves are generated using serial dilutions of polystyrene beads in water at 400, 200, 100, 50, 25, 12.5, 6.25, 3.125, 1.562 and 0 mg/mL. In addition, a mixture containing 160 μL of beads with 40 μL of 40 μM Nile Red solution was incubated for 10 minutes at room temperature. Samples were read at 450 nm by the instrument. As shown in FIG. 2, a linear relationship was obtained with increasing concentration of the beads with a limit of detection (LOD) of 35 μg/mL using the formula $3.3/\sigma$, where $\sigma$ is the standard deviation of the response and S is the slope of the calibration curve. Bead concentrations above 400 μg/mL produced fluorescence signals, but the signals were not linear.

The impact of different incubation times on the slope of the linear regressions was tested. The assay mixture with increasing bead concentrations was incubated for 10, 20, 30, or 60 minutes at room temperature. RFUs were read using the hand-held fluorometer. As shown in FIG. 3, the slope of the linear regression obtained at 620 nm is consistent across different incubation times. Therefore, an incubation time of 10 minutes for subsequent experiments is used for assay optimization.

Figure 4B:
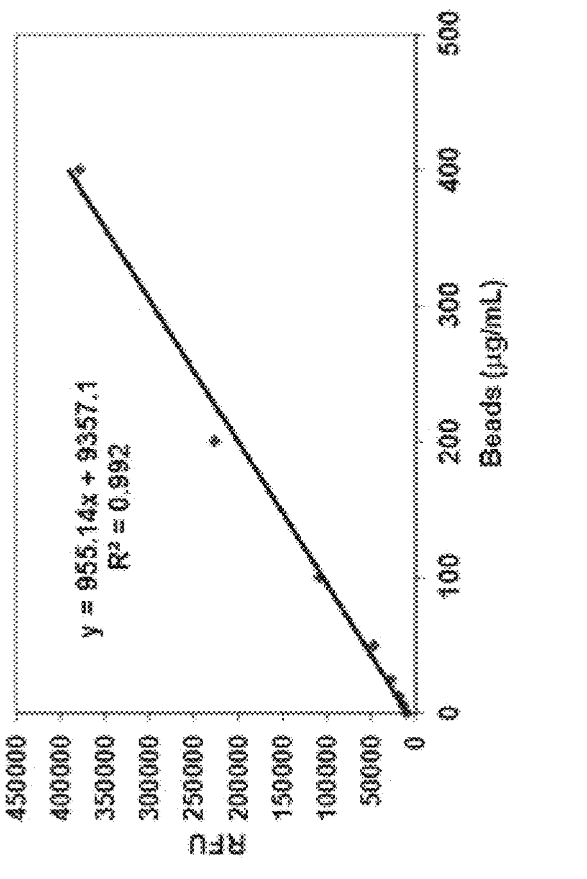
FIG. 4B is a graph showing the effect of shaking the mixture on the calibration curve.
Figure 4A:
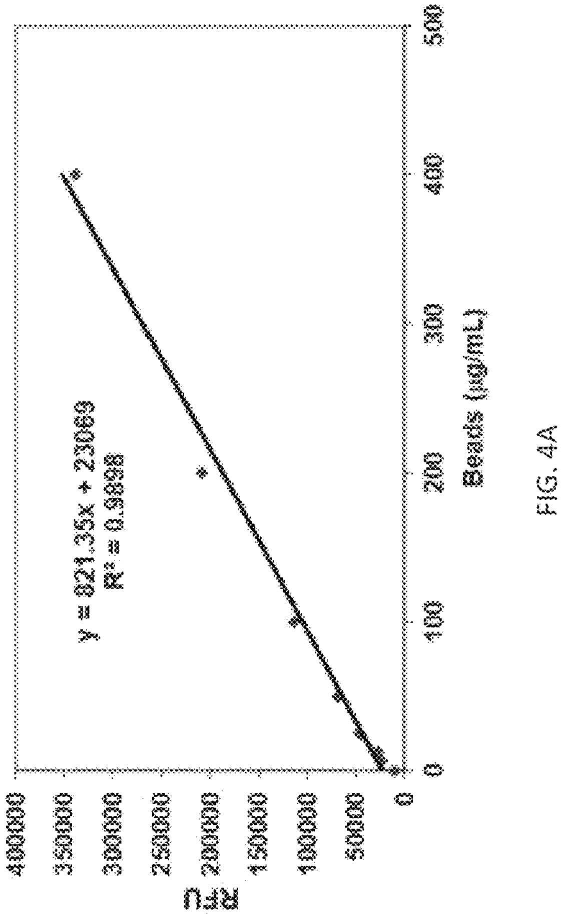
FIG. 4A is a graph showing the effect of not shaking the mixture on the calibration curve.
Figure 5:
FIG. 5 is a schematic of the one-step nanoplastic detection method for water samples.
Figure 5:
Figure 5:
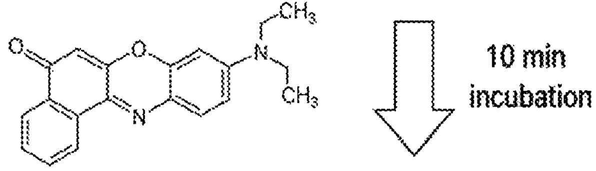
Figure 5:
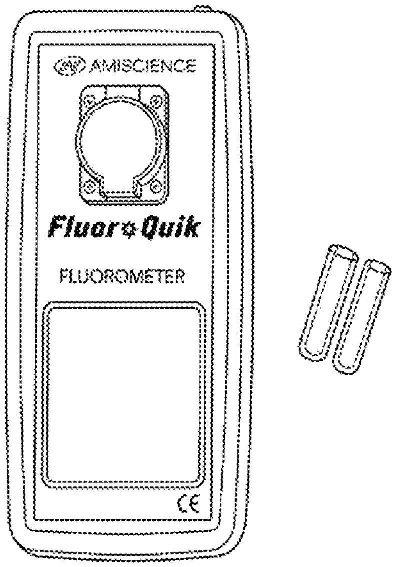

The effect of optimal mixing of the final solution without shaking (FIG. 4A) or with shaking (FIG. 4B) was tested using an orbital shaker. Serial dilutions of bead samples were mixed with Nile Red dye and left on an orbital shaker at 200 rpm. Mixed samples without shaking were left on the benchtop for 10 minutes as control. As shown in FIGS. 4A and 4B, the slope of linear regression obtained by both methods is similar. Based on the optimization of different parameters, the protocol utilized to test nanoplastics in influent and effluent wastewater is shown in FIG. 5.

Sewage water is treated daily at the TriCo Regional Sewer Facility (Zionsville, IN). The plant collects about 4 million gallons of wastewater from the residents in the western half of Carmel, IN, and sections of Indianapolis, IN. Several water parameters are collected daily from influent and effluent water samples to monitor quality when the treated water is allowed back into the Indiana White River. The facility tested influent and effluent water samples collected on five independent days for different parameters and data was provided for this study. As shown in FIGS. 6A and 6B, the effluent samples showed a significant reduction in total suspended solids, total ammonia, and phosphorus content.

Figure 7:
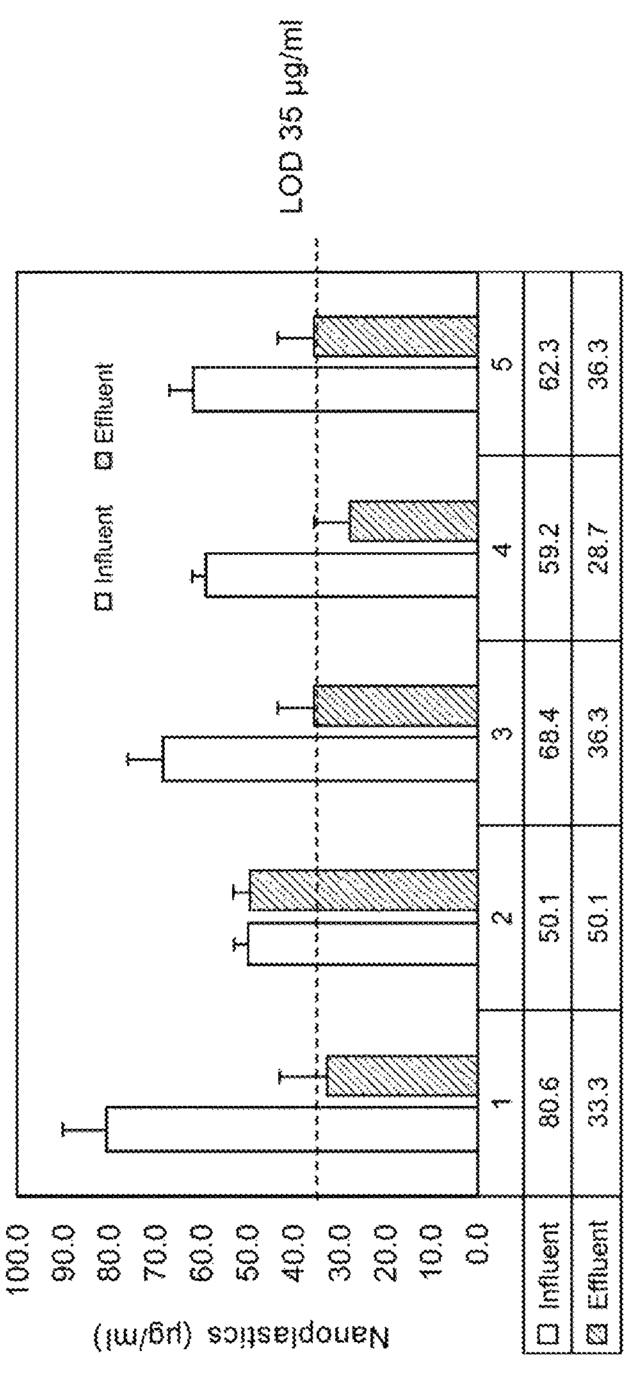
FIG. 7 is a graph showing nanoplastics in influent and effluent wastewater samples.

Nanoplastics levels were measured with the detection method disclosed herein using the fluorometer instrument. First, wastewater samples were filtered using a 0.45 μm syringe filter to remove suspended debris. As described above, 160 μL of filtered wastewater was mixed with 40 μL of Nile Red working solution and incubated for 10 minutes at room temperature before reading at 450 nm. As shown in FIG. 7, nanoplastics were detected from influent samples from all five collection days. On the other hand, a significant reduction of nanoplastics was observed in effluent water samples from four out of five days of collection, which may be due to the trapping of nanoplastics in the sewage sludge waste. In all cases, the levels were near or lower than the limit of detection of the assay. Interestingly, the levels of nanoplastics were similar in the influent and effluent water samples on day two. The data points to the utility of the one-step nanoplastic detection method to monitor plastic load in treated water samples. A comparison of the nanoplastic content of influent samples to the number of particles revealed a high nanoplastic load in all five collection days as shown in FIG. 8.

A one-step nanoplastic detection method using a custom-built portable device has been developed for routine screening of field samples. The additional step of water filtration allows the detection of nanoplastics without the interference of signals from the solid particulate materials with a limit of detection of 35 μg/mL. This method does not require sample shaking, and results can be obtained within 10 minutes, making the method suitable for rapidly detecting hotspots of plastic contamination in water sources. The method technique is intended to serve as a first screen for nanoplastic load in water. The method may be used in wastewater treatment and surface water streams that drain into urban watersheds.

Trico Regional Sewer Utility in Zionsville, Indiana provides efficient sanitary service to the local neighborhoods and businesses by treating millions of gallons of wastewater per day. Trico Regional Sewer Utility operates a wastewater treatment facility consisting of an influent flow meter, three mechanical bar screens, a new grit removal system, eight vertical loop reactors, six secondary clarifiers, phosphorus removal via chemical addition, ultraviolet light disinfection, post aeration with fine bubble diffusers, and effluent flow metering. Sludge management includes five aerobic digesters and a belt filter press. The plant processes are shown in FIG. 9.

Figure 9:
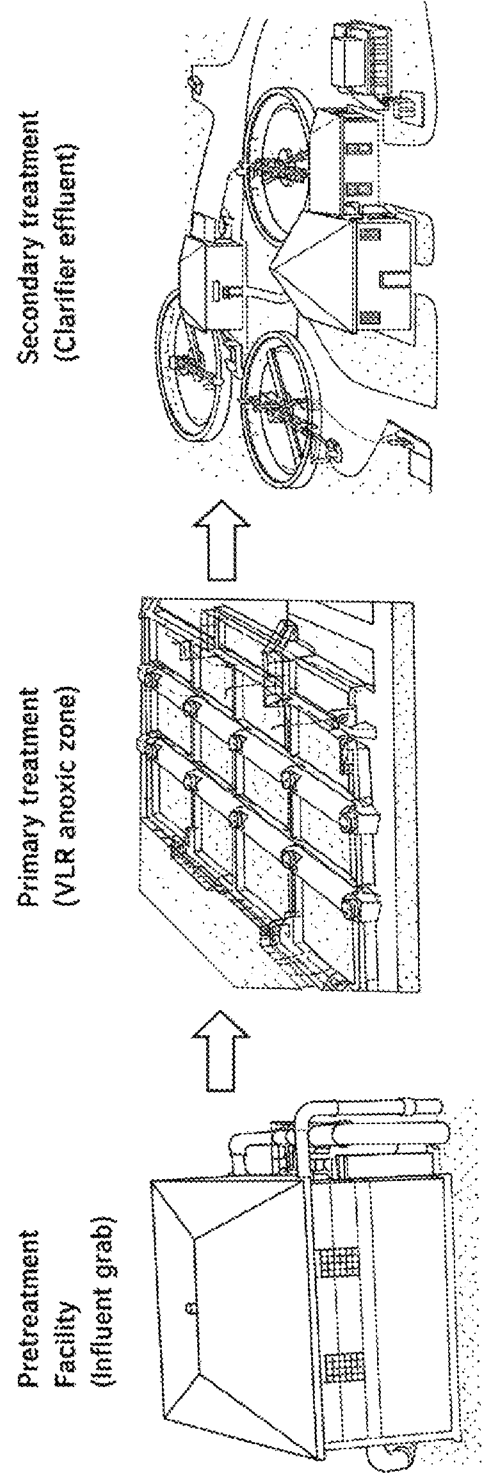
FIG. 9 is a diagrammatic view of plant processes.

As shown in FIG. 9, the first stage of the plant process is pretreatment (Plant Influent). The state-of-the-art pretreatment building accepts all of the sanitary waste via 24 lift stations. It consists of a screening process to remove unwanted and untreatable materials such as plastics and metals. The screenings are conveyed through a screw press to remove the excess water. At the end of the screw press, the screenings are dropped into a hopper then hauled to a landfill.

The pretreatment is where the incoming wastewater stream is measured for flow and sampled to identify the quantity of organic wastes. An odor control system is used to remove harmful gases such as hydrogen sulfide and methane from incoming wastewater stream piping making a safe working environment in the pretreatment building. After pretreatment, the organic material enters into one of two biological treatment methods or activated sludge processes. The current method in use is a Vertical Loop Reactor (VLR). The VLR contains a microbial mass in order to metabolize harmful organic contaminants. Ammonia is an important contaminant to remove by treatment.

As shown in FIG. 9, the secondary treatment consists of six clarifiers. The clarifiers accept the flow from the VLR. The purpose of the secondary treatment is to separate the solids and the water. A clarifier is a circular basin in which effluent from the activated sludge process is held for a period of time during which the heavier biomass (microorganisms) settles to the bottom as activated sludge. This sludge, teaming with hungry microorganisms, can be returned to the first aeration basin to begin the activated sludge treatment process all over again. The solids containing live biological organisms settle to the bottom of the clarifier. The settled solids will then be returned back to biological treatment or permanently removed from the treatment system via pumps. The clear water exits the clarifiers by gravity to the next step of treatment.

Once the clear water has exited the clarifiers, the water travels to disinfection treatment. The method of treatment is ultraviolet light, which destroys the reproductive cells of disease-causing bacteria which inhibits further growth. *E. coli* is the indicator organism that is tested to determine the effectiveness of disinfection. The plant effluent is monitored for flow volume, provided with mechanical air to sustain biological life in the receiving stream and sampled for removal of organic materials.

Figure 10:
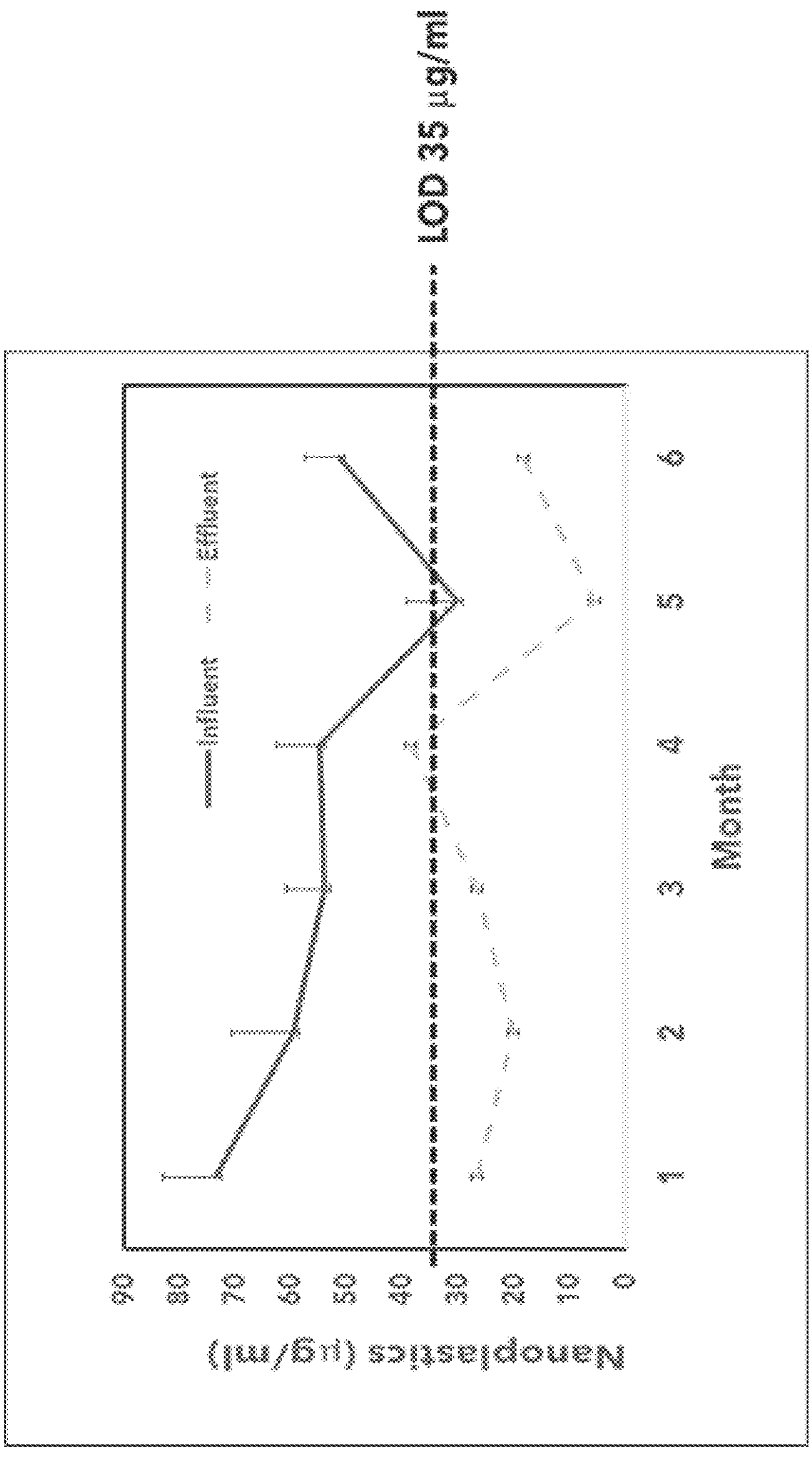
FIG. 10 is a graph showing nanoplastics measured over six months.

Nanoplastics levels in wastewater samples were monitored by collecting influent and effluent water samples on five independent days each month for a period of six consecutive months. Nanoplastics levels were measured using the one-step detection method. Nanoplastics load was consistently higher in the influent wastewater samples compared to effluent water as shown in FIG. 10. This correlated with the increased levels of total suspended solids in influent wastewater in comparison to effluent water as shown in FIG. 11.

Figures 11, 12:
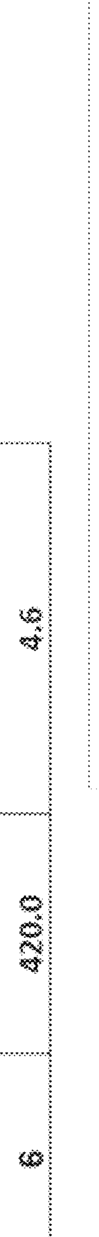
FIG. 11 is a table showing suspended solids per the six months of FIG. 10.
FIG. 12 is a graph showing nanoplastics in influent wastewater samples when water is held in clarifiers prior to exit as effluent water into water streams.

Nanoplastics in influent wastewater samples were effectively removed to below detection levels when water was held in the clarifiers prior to exit as effluent water into the water streams as shown in FIG. 12. The hand-held fluorometer device may be used for routine field based testing and water quality labs to help monitor for the efficiency of wastewater treatment.

The invention claimed is:

1. A method of detecting nanoplastics in water, the method comprising:

providing a 0.45 μm syringe and a 0.45 μm syringe filter, collecting a water sample from the water, wherein the water is wastewater, filtering the water sample with the 0.45 μm syringe and the 0.45 μm syringe filter to remove debris from the water sample to form a filtered water sample, adding a lipophilic fluorescent dye to the filtered water sample to form a mixture, incubating the mixture for an incubation time period at a predetermined temperature, wherein the incubation time period is less than 20 minutes, and measuring a nanoplastics concentration in the mixture using a measurement device at a predetermined wavelength.

2. The method of claim 1, wherein the lipophilic fluorescent dye comprises Nile Red dye.

3. The method of claim 1, wherein the mixture comprises about 20% methanol concentration.

4. The method of claim 1, wherein the incubation time period is about 10 minutes.

5. The method of claim 1, wherein the predetermined wavelength is about 450 nanometers.

6. The method of claim 1, wherein the mixture is not agitated.

7. The method of claim 1, wherein the predetermined temperature is room temperature.

8. The method of claim 1, wherein the 0.45 μm syringe filter comprises hydrophobic polytetrafluoroethylene (PTFE) fluorophore.

9. The method of claim 1, further comprising providing a plurality of Eppendorf tubes.

10. The method of claim 9, further comprising providing a plurality of 1 mL tuberculin syringes.

11. The method of claim 1, further comprising positioning the mixture on an orbital shaker and agitating the mixture with the orbital shaker.

12. The method of claim 1, further comprising powering the measurement device with a 5V DC power adaptor or a plurality of batteries.

* * * * *